United States Patent
Senn-Bilfinger et al.

(10) Patent No.: US 6,936,623 B2
(45) Date of Patent: Aug. 30, 2005

(54) PYRANO[2,3-C]IMIDAZO[-1,2-A]PYRIDINE DERIVATIVES FOR THE TREATMENT OF GASTROINTESTINAL DISORDERS

(75) Inventors: Jörg Senn-Bilfinger, Constance (DE); Wilm Buhr, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/811,496

(22) Filed: Apr. 1, 2004

(65) Prior Publication Data

US 2004/0180920 A1 Sep. 16, 2004

Related U.S. Application Data

(63) Continuation of application No. 10/182,620, filed as application No. PCT/EP01/03510 on Mar. 28, 2001, now abandoned.

(30) Foreign Application Priority Data

Mar. 29, 2000 (EP) .............................. 00106690

(51) Int. Cl.⁷ ..................... A61K 31/437; C07D 491/12

(52) U.S. Cl. .......................................... 514/293; 546/83
(58) Field of Search .............................. 514/293; 546/83

(56) References Cited

U.S. PATENT DOCUMENTS 6,160,119 A * 12/2000 Senn-Bilfinger ............. 546/83

FOREIGN PATENT DOCUMENTS

| WO | WO 95/27714 | 10/1995 |
| WO | WO 98/54188 | 3/1998 |
| WO | WO 98/42707 | 10/1998 |

OTHER PUBLICATIONS

Bundgaard, H. Design of Prodrugs. (1985) Elsevier. Amsterdam–New York–Oxford. pp. 1–3.

* cited by examiner

*Primary Examiner*—Charanjit S. Aulakh
(74) *Attorney, Agent, or Firm*—Nath & Associates PLLC; Joshua B. Goldberg; Sheldon M. McGee

(57) ABSTRACT

Compounds of the formula (I), in which the substituents have the meanings mentioned in the description, are suitable for the prevention and treatment of gastrointestinal diseases.

14 Claims, No Drawings

PYRANO[2,3-C]IMIDAZO[-1,2-A]PYRIDINE DERIVATIVES FOR THE TREATMENT OF GASTROINTESTINAL DISORDERS

This is a Continuation application of U.S. patent application Ser. No. 10/182,620 filed Oct. 1, 2002 now abn which is a 371 of PCT/EP01/03510 filed Mar. 28, 2001 which claims priority to European patent application no. 00106690.1 filed Mar. 29, 2000, the contents of which are hereby incorporated by reference in its entirety.

FIELD OF APPLICATION OF THE INVENTION

The invention relates to novel compounds which are used in the pharmaceutical industry as active compounds for the production of medicaments.

KNOWN TECHNICAL BACKGROUND

International Patent Application WO 95/27714 discloses certain substituted tricyclic imidazo[1,2-a]pyridines which are said to reversibly inhibit gastric acid secretion and to be useful in the prevention and treatment of gastrointestinal inflammatory diseases. International Patent Application WO 98/42707 discloses tetrahydroimidazo[1,2-h][1,7] naphthyridines which shall be suitable for the prevention and treatment of gastrointestinal diseases. WO 98/54188 describes fused dihydropyrans, which are said to be suitable for the treatment of peptic ulcer disorders.

DESCRIPTION OF THE INVENTION

The invention relates to compounds of the formula 1

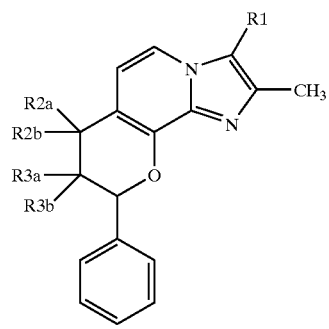

(1)

in which
R1 is methyl or hydroxymethyl,
one of the substituents R2a and R2b is hydrogen and the other is hydroxy, methoxy, ethoxy, propoxy, isopropoxy, butoxy, methoxyethoxy or methoxypropoxy,
one of the substituents R3a and R3b is hydrogen and the other is hydroxy, methoxy, ethoxy, propoxy, isopropoxy, butoxy, methoxyethoxy or methoxypropoxy,
where R2a or R2b on the one hand and R3a or R3b on the other hand are not simultaneously hydroxy,
and their salts.

Suitable salts of compounds of the formula 1 are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

Pharmacologically intolerable salts which can be initially obtained as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula 1 as well as all solvates and in particular all hydrates of the salts of the compounds of formula 1.

The compounds of the formula 1 have three chiral centers. The invention relates to all eight conceivable stereoisomers in any desired mixing ratio with one another, including the pure enantiomers, which are a preferred subject of the invention.

A preferred embodiment of the invention are compounds of the formula 1*

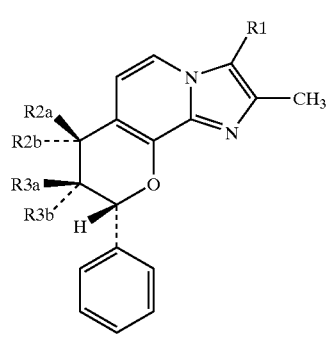

(1*)

in which

R1 is methyl,
one of the substituents R2a and R2b is hydrogen and the other is hydroxy, methoxy, ethoxy, propoxy, isopropoxy, butoxy, methoxyethoxy or methoxypropoxy, Preferred compounds within the scope of the invention are those of embodiment a, which can be characterized by the formula 1**

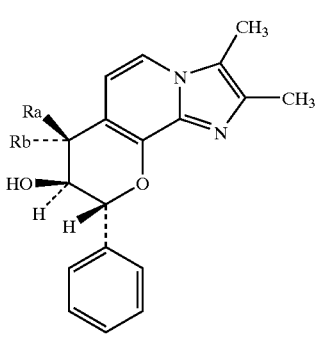

(1**)

in which
one of the substituents Ra and Rb is hydrogen and the other is methoxy, ethoxy, propoxy, isopropoxy, butoxy, methoxyethoxy or methoxypropoxy
and their salts.

Particularly preferred compounds of embodiment a are those of formula 1**, in which
Ra is hydrogen and
Rb is methoxy, ethoxy, propoxy, isopropoxy, butoxy, methoxyethoxy or methoxypropoxy,
and their salts.

With the aid of the general formula 1*, the following exemplary preferred compounds according to the invention may actually be mentioned by means of the substituent meanings for R1, R2a, R2b, R3a and R3b in the following Table 1 (Tab. 1):

TABLE 1

| R1 | R2a | R2b | R3a | R3b |
|---|---|---|---|---|
| $CH_3$ | H | $OCH_3$ | OH | H |
| $CH_3$ | H | $OC_2H_5$ | OH | H |
| $CH_3$ | H | $OC_3H_7$ | OH | H |
| $CH_3$ | H | $OCH(CH_3)_2$ | OH | H |
| $CH_3$ | H | $OC_4H_9$ | OH | H |
| $CH_3$ | H | $OCH_2CH_2OCH_3$ | OH | H |
| $CH_3$ | H | $OCH_2CH_2CH_2OCH_3$ | OH | H |
| $CH_3$ | H | OH | $OCH_3$ | H | one of the substituents R3a and R3b is hydrogen and the other is hydroxy, methoxy, ethoxy, propoxy, isopropoxy, butoxy, methoxyethoxy or methoxypropoxy,
where R2a or R2b on the one hand and R3a or R3b on the other hand are not simultaneously hydroxy,
and their salts.

An embodiment (embodiment a) of the invention are compounds of the formula 1*,
in which
R1 is methyl,
one of the substituents R2a and R2b is hydrogen and the other is methoxy, ethoxy, propoxy, isopropoxy, butoxy, methoxyethoxy or methoxypropoxy,
one of the substituents R3a and R3b is hydrogen and the other is hydroxy,
and their salts.

A further embodiment (embodiment b) of the invention are compounds of the formula 1*,
in which
R1 is methyl,
one of the substituents R2a and R2b is hydrogen and the other is hydroxy,
one of the substituents R3a and R3b is hydrogen and the other is methoxy, ethoxy, propoxy, isopropoxy, butoxy, methoxyethoxy or methoxypropoxy,
and their salts.

A further embodiment (embodiment c) of the invention are compounds of the formula 1*,
in which
R1 is methyl,
one of the substituents R2a and R2b is hydrogen and the other is methoxy, ethoxy, propoxy, isopropoxy, butoxy, methoxyethoxy or methoxypropoxy,
one of the substituents R3a and R3b is hydrogen and the other is methoxy, ethoxy, propoxy, isopropoxy, butoxy, methoxyethoxy or methoxypropoxy,
and their salts.

Preferred compounds of the embodiments a to c are those, in which R3b is hydrogen. In the Examples below, the absolute configuration "R" for both positions 8 and 9 has been assigned to these compounds of formula 1* in which R3b is hydrogen.

Particularly preferred compounds of the embodiments a to c are those, in which R2a and R3b are hydrogen.

| R1 | R2a | R2b | R3a | R3b |
|---|---|---|---|---|
| $CH_3$ | H | OH | $OC_2H_5$ | H |
| $CH_3$ | H | OH | $OC_3H_7$ | H |
| $CH_3$ | H | OH | $OCH(CH_3)_2$ | H |
| $CH_3$ | H | OH | $OC_4H_9$ | H |
| $CH_3$ | H | OH | $OCH_2CH_2OCH_3$ | H |
| $CH_3$ | H | OH | $OCH_2CH_2CH_2OCH_3$ | H |
| $CH_3$ | H | $OCH_3$ | $OCH_3$ | H |
| $CH_3$ | H | $OC_2H_5$ | $OC_2H_5$ | H |
| $CH_3$ | H | $OC_3H_7$ | $OC_3H_7$ | H |
| $CH_3$ | H | $OCH(CH_3)_2$ | $OCH(CH_3)_2$ | H |
| $CH_3$ | H | $OC_4H_9$ | $OC_4H_9$ | H |
| $CH_3$ | H | $OCH_2CH_2OCH_3$ | $OCH_2CH_2OCH_3$ | H |
| $CH_3$ | H | $OCH_2CH_2CH_2OCH_3$ | $OCH_2CH_2CH_2OCH_3$ | H |
| $CH_3$ | $OCH_3$ | H | OH | H |
| $CH_3$ | $OC_2H_5$ | H | OH | H |
| $CH_3$ | $OC_3H_7$ | H | OH | H |
| $CH_3$ | $OCH(CH_3)_2$ | H | OH | H |
| $CH_3$ | $OC_4H_9$ | H | OH | H |
| $CH_3$ | $OCH_2CH_2OCH_3$ | H | OH | H |
| $CH_3$ | $OCH_2CH_2CH_2OCH_3$ | H | OH | H |

-continued

| R1 | R2a | R2b | R3a | R3b |
|---|---|---|---|---|
| $CH_3$ | OH | H | $OCH_3$ | H |
| $CH_3$ | OH | H | $OC_2H_5$ | H |
| $CH_3$ | OH | H | $OC_3H_7$ | H |
| $CH_3$ | OH | H | $OCH(CH_3)_2$ | H |
| $CH_3$ | OH | H | $OC_4H_9$ | H |
| $CH_3$ | OH | H | $OCH_2CH_2OCH_3$ | H |
| $CH_3$ | OH | H | $OCH_2CH_2CH_2OCH_3$ | H |
| $CH_3$ | $OCH_3$ | H | $OCH_3$ | H |
| $CH_3$ | $OC_2H_5$ | H | $OC_2H_5$ | H |
| $CH_3$ | $OC_3H_7$ | H | $OC_3H_7$ | H |
| $CH_3$ | $OCH(CH_3)_2$ | H | $OCH(CH_3)_2$ | H |
| $CH_3$ | $OC_4H_9$ | H | $OC_4H_9$ | H |
| $CH_3$ | $OCH_2CH_2OCH_3$ | H | $OCH_2CH_2OCH_3$ | H |
| $CH_3$ | $OCH_2CH_2CH_2OCH_3$ | H | $OCH_2CH_2CH_2OCH_3$ | H |
| $CH_2OH$ | H | $OCH(CH_3)_2$ | OH | H |
| $CH_2OH$ | H | $O(CH_2)_2CH_3$ | OH | H |
| $CH_2OH$ | H | $O(CH_2)_3CH_3$ | OH | H | and the salts of these compounds.

The compounds according to the invention can be prepared as described for or starting from the compounds disclosed in International Patent Application WO 98/54188. Alternatively, the compounds according to the invention can be prepared as outlined in the following reaction schemes and/or as described exemplary in the following Examples.

Scheme 1:

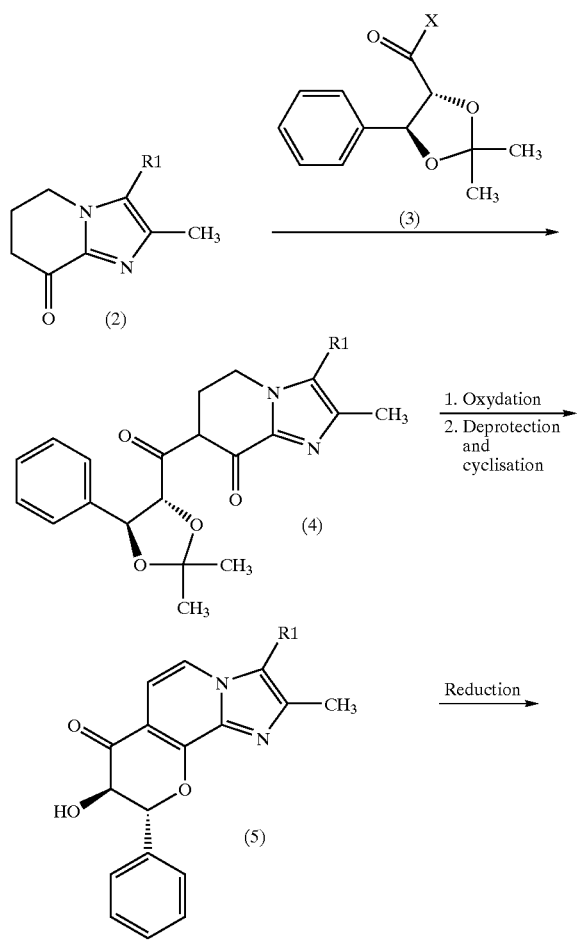

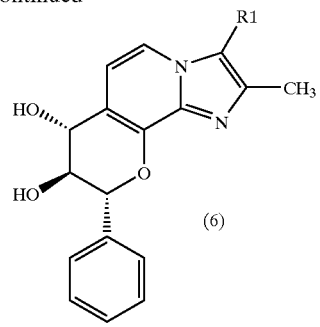

The above scheme 1 represents an example of an enantioselective synthesis of the diol 6, which is subsequently subjected to etherification as described in more detail below.

The group X in compound 3 above is a suitable leaving group, e.g. a halogen atom, preferably a chlorine atom. The acylation is carried out under usual conditions, preferably with using bis-(trimethylsilyl)-sodium or -potassium amide in case that the leaving group is a chlorine atom.

The oxidation following the acylation is carried out under conditions which are known to the expert, using for example chloranil, oxygen or manganese dioxide as oxidation agent. For the subsequent deprotection and cyclisation, special conditions have to be used with regard to the auxiliary acid. Preferably, formic acid is used according to the invention.

The reduction to the diol 6 is also carried out under standard conditions, using for example sodium borohydride as reducing agent. By using sodium borohydride as reducing agent, the 7,8-trans-diol indicated is obtained in over 90% diastereomeric purity. The subsequent etherification which is carried out according to known processes, e.g. as described in the Examples, leads to the final products of formula 1* in which R2a and R3b are hydrogen.

Scheme 2:

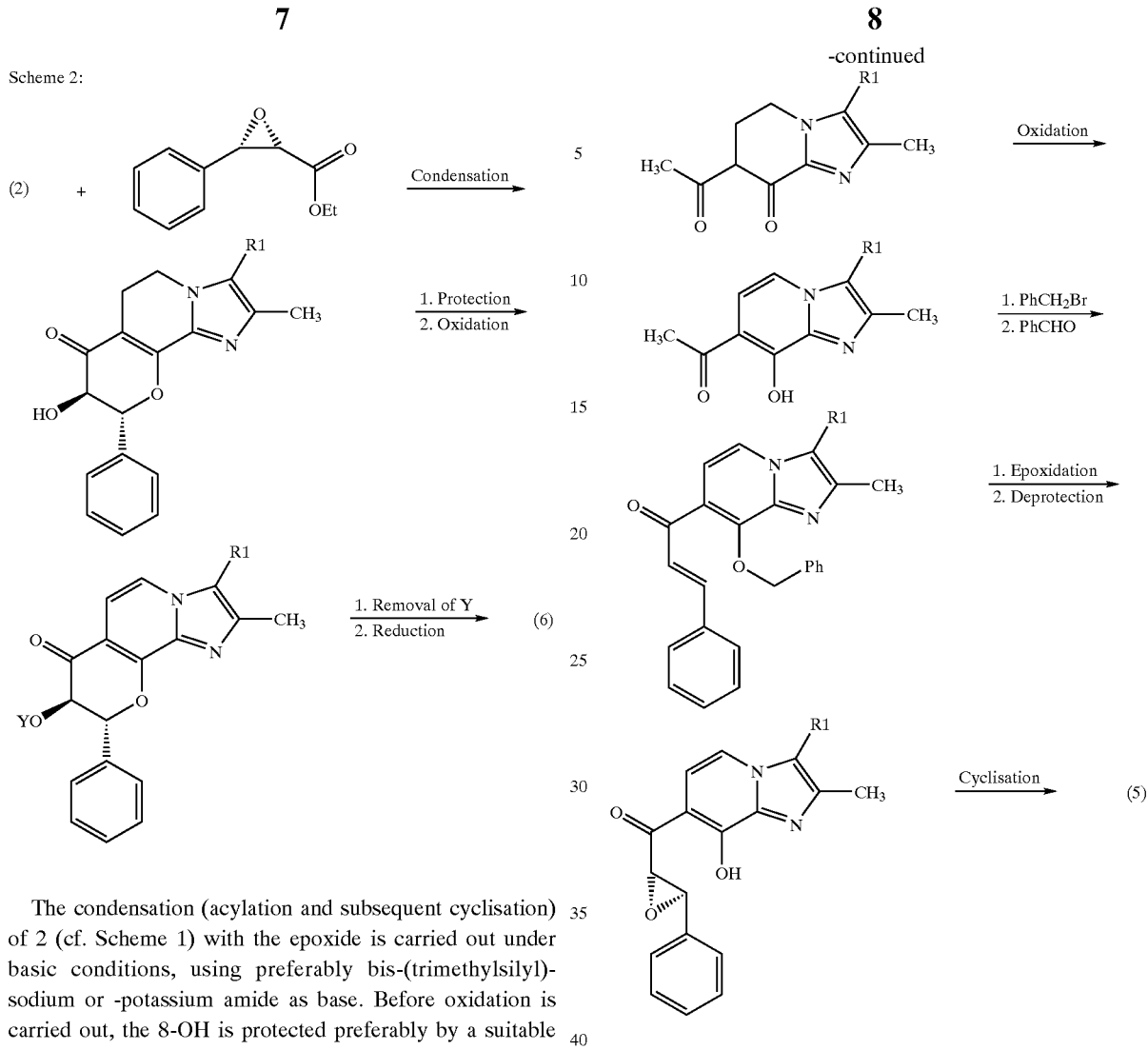

The condensation (acylation and subsequent cyclisation) of 2 (cf. Scheme 1) with the epoxide is carried out under basic conditions, using preferably bis-(trimethylsilyl)-sodium or -potassium amide as base. Before oxidation is carried out, the 8-OH is protected preferably by a suitable protecting group Y, for example by a t-butyl dimethyl silyl group (TBDMS group), by reacting e.g. TBDMSCI with the alcohol under standard conditions.

The following oxidation of the protected compound is carried out under conditions which are known to the expert, using for example chloranil, oxygen or manganese dioxide as oxidation agent.

The reduction to the diol 6 (cf. Scheme 1) is also carried out under standard conditions, using for example sodium borohydride as reducing agent. By using sodium borohydride as reducing agent, the 7,8-trans-diol indicated is obtained in over 90% enantiomeric purity. The subsequent etherification which is carried out according to known processes, e.g. as described in the Examples, leads to the final products of formula 1* in which R2a and R3b are hydrogen.

An additional reaction pathway to obtain compounds of formula 6 (cf. Scheme 1) is outlined in Scheme 3.

Scheme 3:

The acylation of compound 2 (cf. Scheme 1) with acetyl chloride has to be carried out under strongly basic conditions, e.g. by using bis-(trimethylsilylysodium or -potassium amide or lithium diisopropyl amide as base. For the oxidation the same conditions are applicable as outlined for the oxidations described in Schemes 1 and 2. For the protection of the phenolic OH-group a benzyl group is suitable.

The aldol condensation with benzaldehyde is carried out under standard conditions. The epoxidation is also carried out in a manner known per se, using preferably hydrogen peroxide as oxidant under basic conditions.

The deprotection (=split off of the benzyl group) and the subsequent cyclisation are also carried out in a usual manner, the cyclisation being effected under basic conditions. The reduction of compound 5 (cf. Scheme 1) and the subsequent etherification are performed as described in Scheme 1.

The substances according to the invention are isolated and purified in a manner known per se, for example, by distilling off the solvent in vacuo and recrystallizing the residue obtained from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as dichloromethane or chloroform, or a low molecular weight aliphatic alcohol (ethanol, isopropanol) which contains the desired acid, or to which the desired acid is subsequently added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The pure enantiomers, in particular the pure enantiomers of the formula 1*, to which the invention preferably relates, can be obtained in a manner familiar to the person skilled in the art, for example by using pure enantiomers of the intermediates, by enantioselective synthesis (see, for example, the Schemes), by chromatographic separation on chiral separating columns, by derivatization with chiral auxiliary reagents, subsequent separation of diastereomers and removal of the chiral auxiliary group, by salt formation with chiral acids, subsequent separation of the salts and liberation of the desired compound from the salt, or by (fractional) crystallizaton from a suitable solvent. Trans-products obtained (with R2a and R3b=hydrogen) can be converted (at least partly) to the corresponding cis-products (with R2b and R3b=hydrogen) by standing under acidic conditions (e.g. 2 equivalents of acid, such as sulfuric acid) in the corresponding alcohol R2a-OH. Likewise, cis-products obtained can be converted to the corresponding trans-products. The cis- and trans-products are separated e.g. by chromatography or by crystallization.

The following examples serve to illustrate the invention further without restricting it. Likewise, further compounds of the formula 1 whose preparation is not described explicitly can be prepared analogously or in a manner familiar to the person skilled in the art using customary process techniques. The abbreviation min stands for minute(s), h for hour(s), THF for tetrahydrofuran, NaHDMS for sodium hexamethyldisilazane [bis(trimethylsilyl)-sodium amide], TBDMSCI for t-butyl dimethylsilyl chloride and DMAP for 4-dimethylaminopyridine.

In the following examples (Final products) the preparation of pairs of diastereoisomers is described in two successive examples each time. In case of the pairs 7R,8R,9R/7S, 8R,9R, the diastereoisomers can be separated by column chromatography with the 7R,8R,9R diastereoisomers being contained in the first and the 7S,8R,9R diastereoisomer being contained in the second main fraction.

EXAMPLES

Final Products 1. (7R,8R,9R)-2,3-Dimethyl-8-hydroxy-7-(2-methoxyethoxy)-9-phenyl-7H-8,9-dihydro-pyrano-[2,3-c]imidazo[1,2-a]pyridine To a suspension of 1.50 g (4.83 mmol) of (7R,8R,9R)-2,3-dimethyl-7,8-dihydroxy-9-phenyl-7H-8,9-dihydro-pyrano[2,3-c]imidazo[1,2-a]pyridine in 2-methoxy-ethanol (7.0 ml), 0.51 ml (9.67 mmol) of sulfuric acid are added drop by drop. Subsequently the mixture is stirred at 120° C. for 6 h. Afterwards the mixture is diluted with water (100 ml), neutralised With saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 1/1) to give 0.40 g (1.08 mmol/22%) of the title compound as a colourless solid of melting point 155–157° C. (diethyl ether).

2. (7S,8R,9R)-2,3-Dimethyl-8-hydroxy-7-(2-methoxyethoxy)-9-phenyl-7H-8,9-dihydro-pyrano-[2,3-c]imidazo[1,2-a]pyridine To a suspension of 1.50 g (4.83 mmol) of (7R,8R,9R)-2,3-dimethyl-7,8-dihydroxy-9-phenyl-7H-8,9-dihydro-pyrano[2,3-c]imidazo[1,2-a]pyridine in 2-methoxy-ethanol (7.0 ml), 0.51 ml (9.67 mmol) of sulfuric acid are added drop by drop. Subsequently the mixture is stirred at 120° C. for 6 h. Afterwards the mixture is diluted with water (100 ml), neutralised with saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 1/1) to give 0.61 g (1.66 mmol/34%) of the title compound as a colourless solid of melting point 197–199° C. (diethyl ether).

3. (7R,8R,9R)-2,3-Dimethyl-8-hydroxy-7-ethoxy-9-phenyl-7H-8,9-dihydro-pyrano[2,3-c]imidazo-[1,2-a]pyridine To a suspension of 2.00 g (6.44 mmol) of (7R,8R,9R-2,3-dimethyl-7,8-dihydroxy-9-phenyl-7H-8,9-dihydro-pyrano[2,3-c]imidazo[1,2-a]pyridine in ethanol (7.0 ml), 0.69 ml (12.8 mmol) of sulfuric acid are added drop by drop. Subsequently the mixture is stirred in a sealed tube at 100° C. for 8 h. Afterwards the mixture is diluted with water (100 ml), neutralised with saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 7/2) to give 0.15 g (0.44 mmol/7.0%) of the title compound as a colourless solid of melting point 249° C. (diethyl ether).

4. (7S,8R,9R)-2,3-Dimethyl-8-hydroxy-7-ethoxy-9-phenyl-7H-8,9-dihydro-pyrano[2,3-c]imidazo-[1,2-a]pyridine To a suspension of 2.00 g (6.44 mmol) of (7R,8R,9R)-2,3-dimethyl-7,8-dihydroxy-9-phenyl-7H-8,9-dihydro-pyrano[2,3-c]imidazo[1,2-a]pyridine in ethanol (7.0 ml), 0.69 ml (12.8 mmol) of sulfuric acid are added drop by drop. Subsequently the mixture is stirred in a sealed tube at 100° C. for 8 h. Afterwards the mixture is diluted with water (100 ml), neutralised with saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 7/2) to give 0.41 g (1.21 mmol/19%) of the title compound as a colourless solid of melting point 223° C. (diethyl ether).

5. (7R,8R,9R)-2,3-Dimethyl-8-hydroxy-7-(2-methoxypropoxy)-9-phenyl-7H-8,9-dihydro-pyrano-[2,3-c]imidazo[1,2-a]pyridine To a suspension of 2.00 g (6.44 mmol) of (7R,8R,9R-2,3-dimethyl-7,8-dihydroxy-9-phenyl-7H-8,9-dihydro-pyrano

[2,3-c]imidazo[1,2-a]pyridine in 2-methoxy-propanol (10.0 ml), 0.69 ml (12.8 mmol) of sulfuric acid are added drop by drop. Subsequently the mixture is stirred at 140° C. for 7 h. Afterwards the mixture is diluted with water (100 ml), neutralised with saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 7/2) to give 0.15 g (0.39 mmol 16.5%) of the title compound as a colourless solid.

$^1$H-NMR (200 MHz, CDCl$_3$): δ=1.92 (m, 2H), 2.36 (s, 3H), 2.38 (s, 3H), 3.34 (s, 3H), 3.54 (dd, 2H), 3.95 (dd, 2H), 4.21 (dd, 1H), 4.76 (d, 1H), 5.06 (d, 1H), 6.83 (d, 1H), 7.30–7.57 (m, 6H).

6. (7S,8R,9R)-2,3-Dimethyl-8-hydroxy-7-(2-methoxypropoxy)-9-phenyl-7H-8,9-dihydro-pyrano-[2,3-c]imidazo[1,2-a]pyridine To a suspension of 2.00 g (6.44 mmol) of (7R,8R,9R)-2,3-dimethyl-7,8-dihydroxy-9-phenyl-7H-8,9-dihydro-pyrano[2,3-c]imidazo[1,2-a]pyridine in 2-methoxy-ethanol (10.0 ml), 0.69 ml (12.8 mmol) of sulfuric acid are added drop by drop. Subsequently the mixture is stirred at 140° C. for 7 h. Afterwards the mixture is diluted with water (100 ml), neutralised with saturated aqueous sodium hydrogen carbonate solution and extracted twice with dichloromethane. The combined organic layers are washed with brine, dried over sodium sulphate and evaporated in vacuo. The crude product is purified by column chromatography (diethyl ether/triethylamine: 7/2) to give 0.32 g (0.84 mmol/13%) of the title compound as a colourless solid of melting point 209° C. (diethyl ether).

7. (7R,8R,9R)-2,3-Dimethyl-8-hydroxy-7-(2-propoxy)-9-phenyl-7H-8,9-dihydro-pyrano[2,3-c]imidazo[1,2-a]pyridine To a suspension of 2.00 g (6.44 mmol) of (7R,8R,9R)-2,3-dimethyl-7,8-dihydroxy-9-phenyl-7H-8,9-dihydro-pyrano[2,3-c]imidazo[1,2-a]pyridine in propan-2-ol (7.0 ml), 0.51 ml (9.67 mmol) of sulfuric acid are added drop by drop. Subsequently the mixture is stirred in a sealed tube at 100° C. for 7 h. Afterwards the mixture is diluted with water (100 ml), neutralised with saturated aqueous sodium hydrogen carbonate solution and extracted two times with dichloromethane. The combined organic layers are washed with brine, dried over sodium sulphate and evaporated in vacuo. The crude product is purified by column chromatography (diethyl ether/triethylamine: 1/1) to give 0.25 g (0.71 mmol/11%) of the title compound as a colourless solid of melting point 218° C. (diethyl ether).

8. (7S,8R,9R)-2,3-Dimethyl-8-hydroxy-7-(2-propoxy)-9-phenyl-7H-8,9-dihydro-pyrano[2,3-c]imidazo[1,2-a]pyridine To a suspension of 2.00 g (6.44 mmol) of (7R,8R,9R)-2,3-dimethyl-7,8-dihydroxy-9-phenyl-7H-8,9-dihydro-pyrano[2,3-c]imidazo[1,2-a]pyridine in propan-2-ol (7.0 ml), 0.51 ml (9.67 mmol) of sulfuric acid are added drop by drop. Subsequently the mixture is stirred in a sealed tube at 100° C. for 7 h. Afterwards the mixture is diluted with water (100 ml), neutralised with saturated aqueous sodium hydrogen carbonate solution and extracted two times with dichloromethane. The combined organic layers are washed with brine, dried over sodium sulphate and evaporated in vacuo. The crude product is purified by column chromatography (diethyl ether/triethylamine: 1/1) to give 0.28 g (0.79 mmol/12%) of the title compound as a colourless solid of melting point 222° C. (diethyl ether).

9. (7R,8R,9R)-2,3-Dimethyl-8-hydroxy-7-butoxy-9-phenyl-7H8,9-dihydro-pyrano[2,3-c]imidazo[1,2-a]pyridine To a suspension of 2.00 g (6.44 mmol) of (7R,8R,9R)-2,3-dimethyl-7,8-dihydroxy-9-phenyl-7H-8,9-dihydro-pyrano[2,3-c]imidazo[1,2-a]pyridine in butanol (7.0 ml), 0.51 ml (9.67 mmol) of sulfuric acid are added drop by drop. Subsequently the mixture is stirred in a sealed tube at 120° C. for 7 h. Afterwards the mixture is diluted with water (100 ml), neutralised with saturated aqueous sodium hydrogen carbonate solution and extracted two times with dichloromethane. The combined organic layers are washed with brine, dried over sodium sulphate and evaporated in vacuo. The crude product is purified by column chromatography (diethyl ether/triethylamine: 1/1) to give 0.14 g (0.38 mmol/6.0%) of the title compound as a colourless solid of melting point 173° C. (diethyl ether).

10. (7S,8R,9R)-2,3-Dimethyl-8-hydroxy-7-butoxy-9-phenyl-7H-8,9-dihydro-pyrano[2,3-c]imidazo[1,2-a]pyridine To a suspension of 2.00 g (6.44 mmol) of (7R,8R,9R-2,3-dimethyl-7,8-dihydroxy-9-phenyl-7H-8,9-dihydro-pyrano[2,3c]imidazo[1,2-a]pyridine in butanol (7.0 ml), 0.51 ml (9.67 mmol) of sulfuric acid are added drop by drop. Subsequently the mixture is stirred in a sealed tube at 120° C. for 7 h. Afterwards the mixture is diluted with water (100 ml), neutralised with saturated aqueous sodium hydrogen carbonate solution and extracted two times with dichloromethane. The combined organic layers are washed with brine, dried over sodium sulphate and evaporated in vacuo. The crude product is purified by column chromatography (diethyl ether/triethylamine: 1/1) to give 0.40 g (1.09 mmol/17.0%) of the title compound as a colourless solid of melting point 188° C. (diethyl ether).

Starting Compounds

A. 2,3-Dimethyl-6,7-dihydro-5H-imidazo[1,2-a]pyridin-8-one 500 g (2.35 mol) of 8-amino-2,3-dimethyl-imidazo[1,2-a]pyridine (EP-A-299470) and 150 g (10% Pd) palladium on carbon suspended in 6.0 n hydrochloric acid (5.0 l) are stirred under 10 bar pressure of hydrogen at 50° C. for 24 h. The catalyst is filtered off and the reaction mixture is concentrated in vacuo to 2.0 l. This solution is extracted with dichloromethane. The water layer is adjusted with concentrated ammonia solution to pH 4.8–5.0 and extracted again with dichloromethane. This procedure is repeated ten times. The combined organic layers are dried over sodium sulphate and are evaporated. The crude product is crystallised with i-propanol to give 334.1 g of the title compound as light brown crystals with a melting point of 178.5° C. (i-propanol).

B. 2,3-Dimethyl-7-[(2R,3S)-2,3-O,O-isopropylidene-3-phenylpropan-1-on-1-yl]-6,7-dihydro-5H-imidazo[1,2-a]pyridin-8-one To a suspension of 28.50 g (118.4 mmol) of 2,3 dimethyl-6,7-dihydro-5H-imidazo[1,2-a]pyridin-8-one in THF (180 ml), 237.0 ml (1M in THF/60.90 mmol) NaHDMS are added drop by drop at 0° C. The reaction mixture is stirred for 1 h. Subsequently the mixture is cooled to −78° C. and 19.40 g (80.60 mmol) of (2R,3S)-2,3-O,O-isopropylidene-3-phenyl-propionyl chloride is added slowly. The reaction is stirred for 2 h between −70 to −60° C. and warmed up to 25° C. and stirred 4 h again. The reaction is quenched by adding of saturated aqueous ammonium chloride solution (2.0 ml). Subsequently the mixture is concentrated in vacuo. The crude mixture is dissolved in dichlormethane and washed with saturated aqueous ammonium chloride solution, dried over sodium sulphate and evaporated in vacuo. The crude product is purified by crystallisation (i-propanol) to give the title compound as a light yellow solid 23.50 g (63.80 mmol/53%) with a melting point of 195° C. (i-propanol).

C. 2,3-Dimethyl-7-[(2R,3S)-2,3-O,O-isopropylidene-3-phenylpropan-1 n-1-yl]imidazo[1,2-a]-pyridin-8-ol A mixture of 16.80 g (45.60 mmol) of 2,3-dimethyl-7-[(2R,3S)-2,3-O,O-isopropylidene-3-phenylpropan-1-on-1-yl]-6,7-dihydro-5H-imidazo[1,2-a]pyridin-8-one and 12.30 g (50.20 mmol chloranil in dioxane (170 ml) is stirred for 1 h at 100° C. The solvent is evaporated and the crude mixture is stirred with i-propanol. The filtration at 0° C. gives 11.40 g (31.11 mmol/68%) of the title compound as a light green solid with a melting point of 191° C. (i-propanol).

D. (8R,29R)-2,3-Dimethyl-8-formyloxy-9-phenyl-7H-8,9-dihydro-pyrano[2,3-c]imidazo[1,2-a]pyridin-7-one A mixture of 0.50 g (1.36 mmol) of 2,3-dimethyl-7-[(2R,3S)-2,3-O,O-isopropylidene-3-phenylpropan-1-on-1-yl]imidazo[1,2-a]pyridin-8-ol and 0.42 g (0.68 mmol) ammonium formate dissolved in formic acid (10 ml) is stirred at 80° C. for 2 h. Afterwards the acid is removed in vacuo and the residue is dissolved in dichloromethane. The solution is neutralised with saturated aqueous sodium hydrogen carbonate solution, washed with brine, dried over sodium sulphate and evaporated in vacuo. The crude product is purified by column chromatography (diethylether/dichloromethane 8:2) to give the title compound as a light yellow solid (0.26 g, 0.77 mmol/57%) with a melting point of 204° C. (diethylether/dichloromethane).

E. (7R,8R,9R)-2,3-Dimethyl-7,8-dihydroxy-9-phenyl-7H-8,9-dihydro-pyrano[2,3-c]imidazo-[1,2-a]pyridine 1.90 g (5.65 mmol) of (8R,9R)-2,3-dimethyl-8-formyloxy-9-phenyl-7H-8,9-dihydro-pyrano[2,3-c]imidazo[1,2-a]pyridin-7-one is stirred in ethanol at −5° C. During 5 min 0.43 g (11.3 mmol) of NaBH₄ is added and the reaction is warmed up to 10° C. Subsequently saturated aqueous ammonium chloride solution (50 ml) is added. The precipitated solid is separated, washed with water and dried in vacuo at 50° C. to give the title compound as a colourless solid (1.60 g, 5.16 mmol/91%) with a melting point of 130° C. (water)

F. (8R,9R)-2,3-Dimethyl-8-hydroxy-9-phenyl-7H-8,9-dihydro-pyrano[2,3-c]imidazo[1,2-a]pyridin-7-one To 5.00 g (30.50 mmol) of 2,3-dimethyl-6,7-dihydro-5H-imidazo[1,2-a]pyridin-8-one suspended in toluene (50 ml) 6.30 ml (36.60 mmol/20% in ethanol) of sodium ethoxide are added and the mixture is stirred for 30 min. Subsequently 14.1 ml (36.50 mmol) of ethyl-3-phenyl-glycidate is added at −5° C. and the reacton is stirred for a further hour and is then quenched by adding water. The mixture is extracted twice with ethyl acetate and the combined organic layers are washed with brine, dried over sodium sulphate and concentrated under vacuo. The crude product is purified by chromatography (ethyl acetate/diethylether/triethylamine: 1/9/0.2–5/5/0.2) to give the title compound as a light yellow solid (0.30 g, 1.00 mmol/3%) with a melting point of 197° C. (ethyl acetate).

G. (8R,9R)-2,3-Dimethyl-8-(tert-butyl-dimethyl-silyl)-9-phenyl-7H-8,9-dihydro-pyrano[2,3-c]imidazo[1,2-a]pyridin-7-one A solution of 4.00 g (12.90 mmol) of 8R,9R)-2,3-dimethyl-8-hydroxy-9-phenyl-7H-8,9-dihydro-pyrano[2,3-c]imidazo[1,2-a]pyridin-7-one, 5.90 g (38.70 mmol) of TBDMSCI, 2.50 g (38.70 mmol) imidazole and 0.20 g (1.60 mmol) DMAP in dichloromethane is stirred for 18 h at 25° C. The reaction mixture is diluted by adding dichloromethane. The separated organic layer is washed with brine, dried over sodium sulphate and concentrated under vacuo. The crude product is purified by chromatography (diethyl ether/cyclohexane: 8/2) to provide the desired compound as a colourless solid (1.20 g, 2.83 mmol/37%) with a melting point of 213° C. (diethyl ether/cyclohexane).

H. (8R,9R)-2,3-Dimethyl-8-(tert-butyl-dimethyl-silyl)-9-phenyl-7H-8,9-pyrano[2,3-c]imidazo[1,2-a]pyridin-7-one A suspension of 0.25 g (0.59 mmol) of (8R,9R)-2,3-dimethyl-8-(tert-butyl-dimethyl-silyl)-9-phenyl-7H-8,9-dihydro-pyrano[2,3c]imidazo[1,2-a]pyridin-7-one and 2.06 g (23.70 mmol) MnO₂ in dichloromethane (10 ml) is stirred for 120 h at 50° C. The concentrated mixture is suspended in ether and filtered over silica gel. The crude product is purified by chromatography (diethyl ether/cyclohexane: 8/2) to give the title compound as a light yellow solid (0.22 g, 0.52 mmol/88%) with a melting point of 223° C. (diethyl ether/cyclohexane).

I. (8R,9R)-2,3-Dimethyl-8-hydroxy-9-phenyl-7H-8,9-dihydro-pyrano[2,3-c]imidazo[1,2-a]pyridin-7-one 0.50 g (1.18 mmol) of (8R,9R)-2,3-dimethyl-8-(tert-butyl-dimethylsilyl)-9-phenyl-7H-8,9-dihydro-pyrano[2,3-c]imidazo[1,2-a]pyridin-7-one is deprotected with HF/pyridine in pyridine/THF under standard conditions to provide the title compound as a colourless solid with a melting point of 168° C. (ethyl acetate).

Commercial Utility

The compounds of the formula 1 and their salts have useful pharmacological properties which make them commercially utilizable. In particular, they exhibit a marked inhibition of gastric acid secretion and an excellent gastric and intestinal protective action in warm-blooded animals, in particular humans. In this context, the compounds according to the invention are distinguished by a high selectivity of action, an advantageous duration of action, a particularly good enteral activity, the absence of significant side effects and a large therapeutic breadth.

"Gastric and intestinal protection" in this connection is understood as meaning the prevention and treatment of gastrointestinal diseases, in particular of gastrointestinal inflammatory diseases and lesions, and of gastric acid-related diseases in mammals including man (such as, for example, gastric ulcers, duodenal ulcers, gastritis, hyperacidic or medicament-related functional gastropathy, reflux esophagitis, Zollinger-Ellison syndrome, heartburn), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically tolerable salts are outstandingly suitable for use in human and veterinary medicine, where they are used, in particular, for the treatment and/or prophylaxis of disorders of the stomach and/or intestine.

The invention therefore further relates to the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

The invention furthermore relates to medicaments which contain one or more compounds of the formula 1 and/or their pharmacologically tolerable salts.

The medicaments are prepared by processes known per se, which are familiar to the person skilled in the art. As medicaments, the pharmacologically active compounds according to the invention (=active compounds) are employed either as such, or preferably in combination with suitable pharmaceutical auxiliaries or excipients in the form of tablets, coated tablets, capsules, suppositories, patches (e.g. as TTS), emulsions, suspensions or solutions, where the active compound content is advantageously between 0.1 and 95% and where, by the appropriate choice of the auxiliaries and excipients, a pharmaceutical administration form (e.g. a delayed-release form or an enteric form) exactly suited to the active compound and/or to the desired onset and duration of action can be achieved.

The person skilled in the art is familiar, on the basis of his expert knowledge, with auxiliaries or excipients which are suitable for the desired pharmaceutical formulations. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose from approximately 0.01 to approximately 20, preferably 0.05 to 5, in particular 0.1 to 1.5, mg/kg of body weight, if appropriate in the form of several, preferably 1 to 4, individual doses to achieve the desired result. In the case of parenteral treatment, similar or (in particular in the case of intravenous administration of the active compounds), as a rule, lower doses can be used. The optimal dose and manner of administration of the active compounds necessary in each case can easily be determined by any person skilled in the art on the basis of his expert knowledge.

If the compounds according to the invention and/or their salts are to be employed for the treatment of the abovementioned diseases, the pharmaceutical preparations can also contain one or more pharmacologically active constituents of other pharmaceutical groups. Examples which may be mentioned are: tranquilizers (for example from the benzodiazapines group, e.g. diazepam), spasmolytics (e.g. bietamiverine or camylofin), anticholinergics (e.g. oxyphencyclimine or phencarbamide), local anesthetics (e.g. tetracaine or procaine), and, if appropriate, also enzymes, vitamins or amino acids.

To be emphasized in this connection, in particular, is the combination of the compounds according to the invention with pharmaceuticals which inhibit acid secretion, such as, for example, H2 blockers (e.g. cimetidine, ranitidine), H+/K+-ATPase inhibitors (e.g. omeprazole, pantoprazole), or furthermore with so-called peripheral anticholinergics (e.g. pirenzepine, telenzepine), and with gastrin antagonists with the aim of increasing the main action in an additive or superadditive sense and/or of eliminating or decreasing the side effects, or furthermore the combination with antibacterially active substances (e.g. cephalosporins, tetracyclines, penicillins, macrolides, nitroimidazoles or alternatively bismuth salts) for the control of *Helicobacter pylori*. Antibacterially active combination components which may be mentioned are, for example, meziocillin, ampicillin, amoxycillin, cefalothin, cefoxitin, cefotaxime, imipenem, gentamycin, amikacin, erythromycin, ciprofloxacin, metronidazole, ciarithromycin, azithromycin and combinations thereof (e.g. clarithromycin+metronidazole).

Pharmacology

The excellent gastric protective action and the gastric acid secretion-inhibiting action of the compounds according to the invention can be demonstrated in animal experimental models. The compounds according to the invention investigated in the model mentioned below have been provided with numbers which correspond to the numbers of these compounds in the examples.

Testing of the Secretion-inhibiting Action on the Perfused Rat Stomach

Table A below shows the effects of the compounds according to the invention on the pentagastrin-stimulated acid secretion of the perfused rat stomach in vivo after intravenous administration.

TABLE A

| No. | Dose (µmol/kg) i.v. | Inhibition of acid secretion (%) |
|---|---|---|
| 1 | 1 | 100 |
| 3 | 1 | 100 |

Methodology

The abdomen of anesthetized rats (CD rat, female, 200–250 g; 1.5 g/kg i.m. urethane) was opened after tracheotomy by means of a median upper abdominal incision and a PVC catheter was fixed transorally in the esophagus and another via the pylorus such that the ends of the tube just projected into the gastric lumen. The catheter leading from the pylorus led outwards into the right abdominal wall through a side opening.

After thorough rinsing (about 50–100 ml), warm physiological NaCl solution at 37° C. was continuously passed through the stomach (0.5 ml/min pH 6.8–6.9; Braun-Unita I). The pH (pH meter 632, glass electrode EA 147; φ=5 mm, Metrohm) and, by titration with a freshly prepared 0.01 N NaOH solution to pH 7 (Dosimat 665 Metrohm), the secreted HCl were determined in the effluent in each case collected at an interval of 15 minutes.

The gastric secretion was stimulated by continuous infusion of 1 µg/kg (=1.65 ml/h) of i.v. pentagastrin (left femoral vein) about 30 min after the end of the operation (i.e. after determination of 2 preliminary fractions). The substances to be tested were administered intravenously in 1 ml/kg liquid volumes 60 min after the start of the pentagastrin continuous infusion.

The body temperature of the animals was kept at a constant 37.8–38° C. by infrared irradiation and heat pads (automatic, stepless control by means of a rectal temperature sensor).

What is claimed is:

1. A compound of the formula 1

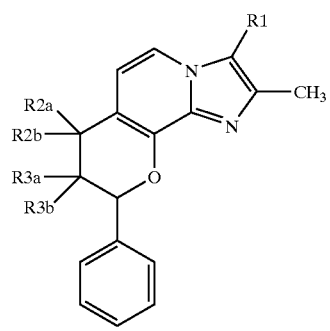

(1)

in which R1 is methyl or hydroxymethyl, one of the substituents R2a and R2b is hydrogen and the other is hydroxy, methoxy, ethoxy, propoxy, isopropoxy, butoxy, methoxyethoxy or methoxypropoxy, one of the substituents R3a and R3b is hydrogen and the other is hydroxy, methoxy, ethoxy, propoxy, isopropoxy, butoxy, methoxyethoxy or methoxypropoxy, where R2a or R2b on the one hand and R3a or R3b on the other hand are not simultaneously hydroxy, or a hydrate, solvate, salt, hydrate of a salt or solvate of a salt thereof.

2. A compound according to claim 1, having the formula 1*

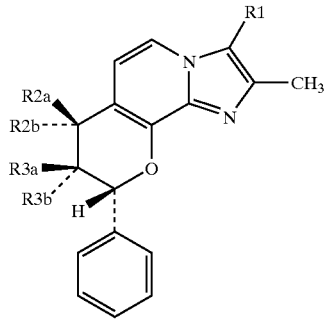

(1*)

in which R1 is methyl or hydroxymethyl, one of the substituents R2a and R2b is hydrogen and the other is hydroxy, methoxy, ethoxy, propoxy, isopropoxy, butoxy, methoxyethoxy or methoxypropoxy, one of the substituents R3a and R3b is hydrogen and the other is hydroxy, methoxy, ethoxy, propoxy, isopropoxy, butoxy, methoxyethoxy or methoxypropoxy, where R2a or R2b on the one hand and R3a or R3b on the other hand are not simultaneously hydroxy, or a hydrate, solvate, salt, hydrate of a salt or solvate of a salt thereof.

3. A compound of formula 1* according to claim 2, in which R1 is methyl, one of the substituents R2a and R2b is hydrogen and the other is methoxy, ethoxy, propoxy, isopropoxy, butoxy, methoxyethoxy or methoxypropoxy, one of the substituents R3a and R3b is hydrogen and the other is hydroxy, or a hydrate, solvate, salt, hydrate of a salt or solvate of a salt thereof.

4. A compound of formula 1* according to claim 2, in which

R1 is methyl, one of the substituents R2a and R2b is hydrogen and the other is methoxy, ethoxy, propoxy, isopropoxy, butoxy, methoxyethoxy or methoxypropoxy, one of the substituents R3a and R3b is hydrogen and the other is methoxy, ethoxy, propoxy, isopropoxy, butoxy, methoxyethoxy or methoxypropoxy, or a hydrate, solvates, salt, hydrate of a salt or solvate of a salt thereof.

5. A compound of formula 1* according to claim 2 in which R3b is hydrogen, or a hydrate, solvate, salt, hydrate of a salt or solvate of a salt thereof.

6. A compound of formula 1* according to claim 2 in which R2a and R3b are hydrogen, or a hydrate, solvate, salt, hydrate of a salt or solvate of a salt thereof.

7. A compound according to claim 1, having the formula 1**

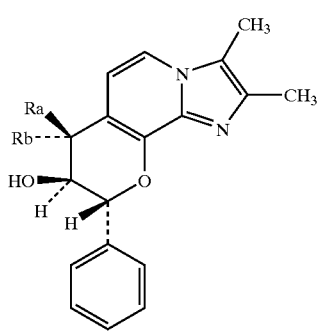

(1**)

in which one of the substituents Ra and Rb is hydrogen and the other is methoxy, ethoxy, propoxy, isopropoxy, butoxy, methoxyethoxy or methoxypropoxy,
or a hydrate, solvate, salt, hydrate of a salt or solvate of a salt thereof.

8. A compound according to claim 1 which is (7R,8R,9R)-2,3-Dimethyl-8-hydroxy-7-(2-methoxyethoxy)-9-phenyl-7H-8,9-dihydropyrano[2,3-c]imidazo[1,2-a]pyridine,
or a hydrate, solvate, salt, hydrate of a salt or solvate of a salt thereof.

9. A pharmaceutical composition comprising a compound as claimed in claim 1 and/or a pharmacologically tolerable hydrate, solvate, salt, hydrate of a salt or solvate of a salt thereof, together with a pharmaceutically acceptable auxiliary and/or excipient.

10. A method of treating a gastrointestinal disease in a patient comprising administering to a patient in need thereof a therapeutically effective amount of a compound as claimed in claim 1 or a pharmaceutically acceptable hydrate, solvate, salt, hydrate of a salt or solvate of a salt thereof, wherein said gastrointestinal disease is selected from the group consisting of gastric ulcers, duodenal ulcers, gastritis, hyperacidic or medicament-related functional gastropathy, reflux esophagitis, Zollinger-Ellison syndrome and heartburn.

11. A compound of formula 1* according to claim 3 in which R3b is hydrogen, or a hydrate, solvate, salt, hydrate of a salt or solvate of a salt thereof.

12. A compound of formula 1* according to claim 4 in which R3b is hydrogen, or a hydrate, solvate, salt, hydrate of a salt or solvate of a salt thereof.

13. A compound of formula 1* according to claim 3 in which R2a and R3b are hydrogen, or hydrate, solvate, salt, hydrate of a salt or solvate of a salt thereof.

14. A compound of formula 1* according to claim 4 in which R2a and R3b are hydrogen, or a hydrate, solvate, salt, hydrate of a salt or solvate of a salt thereof.

* * * * *

UNITED STATES PATENT AND TRADEMARK OFFICE
CERTIFICATE OF CORRECTION

PATENT NO. : 6,936,623 B2
DATED : August 30, 2005
INVENTOR(S) : Senn-Bilfinger et al.

It is certified that error appears in the above-identified patent and that said Letters Patent is hereby corrected as shown below:

Column 18,
Line 59, please delete "solvates" and replace with -- solvate --.

Signed and Sealed this

Eighteenth Day of October, 2005

JON W. DUDAS
*Director of the United States Patent and Trademark Office*